United States Patent [19]

Chakrin et al.

[11] 4,032,652

[45] June 28, 1977

[54] SUBSTITUTED 2H-PYRAN-2,6(3H)-DIONE DERIVATIVES, PHARMACEUTICAL COMPOSITIONS COMPRISING SUCH DERIVATIVES AND METHODS OF INHIBITING THE ANTIGEN-ANTIBODY REACTION

[75] Inventors: Lawrence W. Chakrin, Haddonfield, N.J.; Kenneth M. Snader, Hatboro, Pa.; Chester R. Willis, Kingston, British W. Indies

[73] Assignee: SmithKline Corporation, Philadelphia, Pa.

[22] Filed: Apr. 30, 1976

[21] Appl. No.: 682,001

Related U.S. Application Data

[63] Continuation-in-part of Ser. No. 570,896, April 23, 1975, abandoned, which is a continuation-in-part of Ser. No. 492,640, July 29, 1974, abandoned.

[52] U.S. Cl. .............................. 424/283; 260/345.9
[51] Int. Cl.[2] ................ A61K 31/35; C07D 309/20
[58] Field of Search ................. 424/283; 260/345.9

[56] References Cited

UNITED STATES PATENTS

| 3,849,565 | 11/1974 | Pfister et al. | 424/283 |
| 3,864,493 | 2/1975 | Cairns et al. | 424/283 |
| 3,879,544 | 4/1975 | Reisner et al. | 424/337 |

OTHER PUBLICATIONS

Physician's Desk Reference (PDR), 1974, 28th Edition, pp. 760–761.
R. H. Wiley et al., J. Org. Chem. 21, 686–688, (1956).
A. K. Kiang et al., J. Chem. Soc. (C), 2721–2726, (1971).

*Primary Examiner*—Norman A. Drezin
*Attorney, Agent, or Firm*—Richard D. Foggio; William H. Edgerton

[57] ABSTRACT

Substituted 2H-pyran-2,6(3H)-dione derivatives, pharmaceutical compositions comprising such derivatives and methods of inhibiting the antigen-antibody reaction by administering said compositions. The active ingredients are the products formed by the reaction of acetonedicarboxylic acid with acetic anhydride followed by reaction with an appropriate amine. Certain of the dione derivatives are novel compounds per se.

21 Claims, No Drawings

SUBSTITUTED 2H-PYRAN-2,6(3H)-DIONE DERIVATIVES, PHARMACEUTICAL COMPOSITIONS COMPRISING SUCH DERIVATIVES AND METHODS OF INHIBITING THE ANTIGEN-ANTIBODY REACTION

This application is a continuation-in-part of application Ser. No. 570,896 filed Apr. 23, 1975, now abandoned, which is a continuation-in-part of application Ser. No. 492,640 filed July 29, 1974, now abandoned.

This invention relates to substituted 2H-pyran-2,6(3H)-dione derivatives, pharmaceutical compositions comprising such derivatives which inhibit the antigen-antibody reaction and to methods of inhibiting the antigen-antibody reaction by administering said compositions.

The substituted 2H-pyran-2,6(3H)-dione derivatives which comprise the active ingredient of the pharmaceutical compositions of this invention, in association with a nontoxic pharmaceutical carrier or diluent, are represented by the following general structural formula:

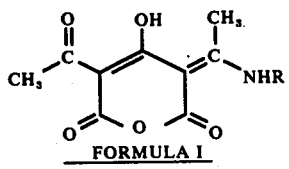

FORMULA I wherein R represents lower alkyl, straight or branched chain, of from 3 to 6 carbon atoms, phenyl, halophenyl such as chlorophenyl, bromophenyl or fluorophenyl, hydroxyphenyl, methoxyphenyl, alkanoyloxyphenyl, the alkanoyl moiety having from 2 to 7 carbon atoms, carbamoyloxyphenyl, N-methylcarbamoyloxyphenyl, N-benzylcarbamoyloxyphenyl, N,N-dimethylcarbamoyloxyphenyl, p-mercaptophenyl, aminophenyl, alkanoylaminophenyl, the alkanoyl moiety having from 2 to 5 carbon atoms, ureidophenyl or carboxymethyleneoxyphenyl.

Advantageously the compositions of this invention comprise a compound of formula I above when R is n-propyl, p-mercaptophenyl, hydroxyphenyl, p-acetoxyphenyl, p-pentanoyloxyphenyl, p-aminophenyl, m-alkanoylaminophenyl or p-ureidophenyl. Preferably R is p-hydroxyphenyl.

In our earlier filed application Ser. No. 492,640 the active ingredient of the pharmaceutical compositions was described as a 5-substituted carbamyldehydroacetic acid. However we also disclosed that Kiang, A. K. et al. *J. Chem. Soc.* (c) pp. 2721–6 (1971) questioned the structure assigned by previous authors such as Wiley, R. H. et al. *J. Org. Chem.* 21:686–688 (1956) to the reaction product of acetonedicarboxylic acid and acetic anhydride, designated 5-carboxydehydroacetic acid, and the carbamyl derivatives thereof. Thus, Kiang et al. supra reported that the reaction of acetonedicarboxylic acid with acetic anhydride gave the compound of structure II and that the latter reacted with aniline to form the compound of structure III:

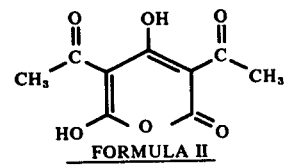

FORMULA II

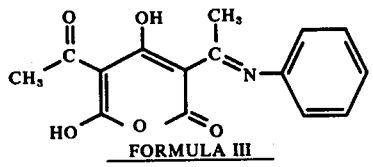

FORMULA III

In view of these facts we stated in said earlier application that we could not discount that the 5-substituted carbamyldehydroacetic acids could have the isomeric structure indicated by Kiang et al.

Upon subsequent investigation which has included $^{13}C$ nuclear magnetic resonance spectral and x-ray crystallographic studies, we have now arrived at the following conclusions. The reaction of acetonedicarboxylic acid with acetic anhydride gives a product having the tautomeric structure as shown below:

A.

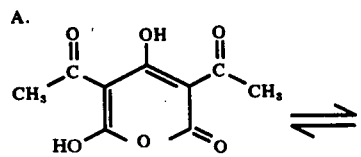 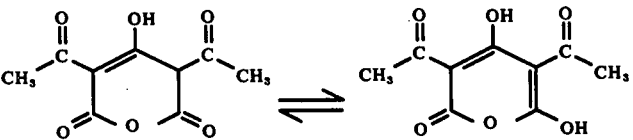

For convenience this product is designated herein as 3,5-diacetyl-4,6-dihydroxy-2H-pyran-2-one. This agrees with Kiang et al's gross structure indicated by formula II above. The rate of tautomerization represented by A above is affected, among other factors, by the solvent used in the $^{13}C$ spectral study. Accordingly the reaction of this product with an amine, $RNH_2$, gives a product having the tautomeric structures as shown below:

B.

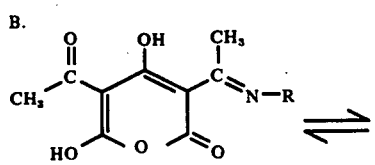 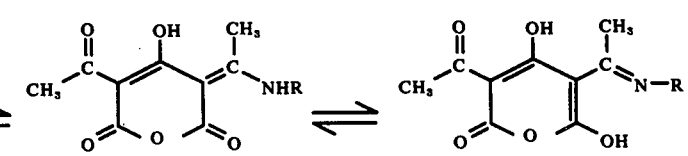

in which R is as defined above for formula I. This also agrees with Kiang et al's gross structure indicated by formula III above.

Although we have not been able to identify by $^{13}C$ nmr the exact tautomer represented by B in solution, an X-ray crystallographic study in solid form of the compound wherein R is p-hydroxyphenyl showed that because of extensive conjugation the carbon-carbon bonds throughout the molecule are hybridized and therefore the bond lengths lie somewhere between the values for double and single bonds. However, since one of the exchangeable hydrogens in this compound is located on the nitrogen, for convenience we have chosen to use one tautomeric form, namely the intermediate enamine pyran-2,6-dione structure, to represent all of the compounds formed by reaction of A with an amine, RNH$_2$, as indicated by formula I above. It will be apparent however to one skilled in the art that the more complete representation of the compounds of formula I is shown by the tautomerization B.

As indicated above the starting material represented by A is obtained by reaction of acetonedicarboxylic acid and acetic anhydride, carried out in sulfuric acid at elevated temperature. This material and the amine, RNH$_2$, are usually heated at reflux in an inert organic solvent such as benzene, toluene or methanol for from two to twelve hours to give the products of formula I. Mono-and di-alkali metal salts of the compounds of formula I, such as the mono-and di-sodium or potassium salts are readily obtainable by treatment with the appropriate alkali metal alkoxide, for example methoxide, in an alkanol solvent such as methanol.

Several products of the reaction of "5-carboxydehydroacetic acid", now known to be the structure represented by A, with amines have been reported by Wiley et al. supra and similarly, Kiang et al. supra has disclosed such reaction products as "anils". However no biological utility has been described for any of these products.

Certain of the compounds of formula I are novel compounds and as such form a part of this invention. These compounds may be represented by the following formula:

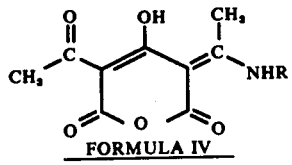

FORMULA IV wherein R represents lower alkyl, straight or branched chain, of from 3 to 6 carbon atoms, hydroxyphenyl, alkanoyloxyphenyl, the alkanoyl moiety having from 2 to 7 carbon atoms, carbamoyloxyphenyl, N-methylcarbamoyloxyphenyl, N-benzylcarbamoyloxyphenyl, N,N-dimethylcarbamoyloxyphenyl, p-mercaptophenyl, aminophenyl, alkanoylaminophenyl, the alkanoyl moiety having from 2 to 5 carbon atoms, ureidophenyl or carboxymethyleneoxyphenyl.

The compounds wherein R is alkanoyloxyphenyl are conveniently prepared from the corresponding hydroxyphenyl derivative by reaction with the appropriate alkanoyl chloride, preferably in an organic base such as triethylamine and a nonreactive solvent such as tetrahydrofuran.

The pharmaceutical compositions of this invention inhibit the release and/or formation of pharmacologically active mediators from effector cells triggered by the interaction of antigen and a specific antibody fixed to the cell surface. Thus the compositions are valuable in the treatment of allergic diseases such as asthma, rhinitis and urticaria.

The inhibitory activity of the compositions of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-N-Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The compounds of formula I administered intravenously to rats at doses of from 0.25 to 10 mg/kg produce marked inhibition of the PCA reaction. A preferred compound, 5-acetyl-4-hydroxy-3-[1-(p-hydroxyphenylamino)-ethylidene]-2H-pyran-2,6(3H)-dione, produced 73% inhibition of the rat PCA wheal at 5.0 mg/kg, i.v. Another preferred compound, 5-acetyl-4-hydroxy-3-[1-(p-mercaptophenylamino)ethylidene]-2-H-pyran-2,6(3H)-dione, produced 100% inhibition of the rat PCA wheal at 5.0 mg/kg, i.v. Similarly 5-acetyl-3-[1-(p-aminophenylamino)ethylidene]-4-hydroxy-2H-pyran-2,6(3H)-dione produced 58% inhibition of the rat PCA wheal at 0.5 mg/kg, i.v.

In testing for mechanism of action, the compounds of formula I were found not to provide comparable inhibition of wheals of equal severity produced in rats by the intracutaneous administration of histamine and serotonin following i.v. administration of the test compound at the same dose and pretreatment time which exhibited significant inhibition of the rat 48-hour PCA reaction.

Upon oral administration, 5-acetyl-4-hydroxy-3-[1-(p-hydroxyphenylamino)ethylidene]-2H-pyran-2,6(3H)-dione produced 58% inhibition in the rat 48 hour PCA system at 25 mg/kg and a pretreatment time of 15 minutes. This compound is also active in vitro for inhibition of antigen induced mediator release from monkey lung and skin and rat lung systems at concentrations of $3.3 \times 10^{-4}$M to $3.3 \times 10^{-6}$M. Similarly 5-acetyl-3-[1-(p-aminophenylamino)ethylidene]-4-hydroxy-2H-pyran-2,6(3H)-dione upon oral administration produced 32% inhibition in the rat 48 hour PCA system at 25 mg/kg and a pretreatment time of 5 minutes.

The pharmaceutical compositions of this invention comprise an appropriate amount of a substituted 2H-pyran-2,6(3H)-dione derivative as set forth in formula I in association with a pharmaceutical carrier or diluent. The nature of the composition and the pharmaceutical carrier or diluent will of course depend upon the intended route of administration, i.e. orally, parenterally or by inhalation. Preferably the active medicament is administered to an animal in a composition comprising an amount sufficient to produce an inhibition of the antigen-antibody reaction. When employed in this manner, the dosage of composition is such that from 0.5 mg to 500 mg of active ingredient are administered at each administration. Advantageously equal doses will be administered 1 to 4 times daily with the daily dosage regimen being about 0.5 mg to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg to about 1 g. If a liquid carrier is used, the preparation will be in the form of a syrup, emulsion, soft gelatin capsule, sterile injectable liquid such as an ampule, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The method in accordance with this invention also includes inhibiting the effects of the antigen-antibody reaction which comprises the prior application to the area of the antigen-antibody mechanism a therapeutically effective amount of a substituted 2H-pyran-2,6(3H)-dione as defined in formula I. A particular application is a method of relieving or preventing allergic airway obstruction which comprises administering to an animal a therapeutically effective amount at suitable intervals.

The pharmaceutical preparations are made following the conventional techniques of the pharmaceutical chemist involving mixing, granulating and compressing when necessary, or variously mixing and dissolving the ingredients as appropriate to the desired end product.

The accompanying examples illustrate the preparation of compounds of formula I and their incorporation into pharmaceutical compositions of this invention and as such are not to be considered as limiting the invention set forth in the claims appended hereto.

EXAMPLE 1

To a boiling solution of 4.2 g. (0.02 m.) of 3,5-diacetyl-4,6-dihydroxy-2H-pyran-2-one in 150 ml. of benzene/methanol is added 1.2 g. (0.02 m.) of n-propylamine and the resulting mixture is refluxed overnight. The reaction mixture is concentrated, filtered and the solid treated with water to give pure 5-acetyl-4-hydroxy-3-[1-(n-propylamino)ethylidene]-2H-pyran-2,6(3H)-dione, m.p. 145°–148° C.

Similarly, 1.8 g. (0.025 m.) of n-butylamine and 5.3 g. (0.025 m.) of 3,5-diacetyl-4,6-dihydroxy-2H-pyran-2-one are refluxed overnight in 50 ml. of benzene and the resulting solid filtered to give 5-acetyl-3-[1-(n-butylamino)ethylidene]-4-hydroxy-2H-pyran-2,6(3H)-dione, m.p. 112°–114° C.

EXAMPLE 2

To a boiling solution of 4.2 g. (0.02 m.) of 3,5-diacetyl-4,6-dihydroxy-2H-pyran-2-one in 150 ml. of benzene is added 2.0 g. (0.02 m.) of n-hexylamine and the mixture is concentrated and the oily residue is triturated with petroleum-ether to give 5-acetyl-3-[1-(n-hexylamino)ethylidene]-4-hydroxy-2H-pyran-2,6(3H)-dione, m.p. 80°–82° C.

EXAMPLE 3

3,5-Diacetyl-4,6-dihydroxy-2H-pyran-2-one (5.3 g.) is dissolved in 200 ml. of boiling toluene and an equimolar amount of p-chloroaniline is added. The mixture is refluxed for 12 hours, cooled and filtered to yield 5-acetyl-3-[1-(p-chlorophenylamino)ethylidene]-4-hydroxy-2H-pyran-2,6(3H)-dione, m.p. 205°–206° C.

EXAMPLE 4 o-Chloroaniline (2.55 g., 0.02 m.) is added to 4.24 g. (0.02 m.) of 3,5-diacetyl-4,6-dihydroxy-2H-pyran-2-one in 150 ml. of methanol and the mixture is refluxed overnight. The reaction mixture is concentrated, cooled and filtered to give 5-acetyl-3-[1-(o-chlorophenylamino)ethylidene]-4-hydroxy-2H-pyran-2,6(3H)-dione, m.p. 143°–145° C.

Similarly, equimolar amounts of m-chloroaniline and 3,5-diacetyl-4,6-dihydroxy-2H-pyran-2-one are refluxed in methanol to afford, after workup, 5-acetyl-3-[1-(m-chlorophenylamino)ethylidene]-4-hydroxy-2H-pyran-2,6(3H)-dione, m.p. 163°–164° C.

EXAMPLE 5

To a boiling solution of 4.24 g. (0.02 m.) of 3,5-diacetyl-4,6-dihydroxy-2H-pyran-2-one in 200 ml. of methanol is added 2.18 g. (0.02 m.) of p-hydroxyaniline. The resulting mixture is refluxed overnight and filtered to yield 5-acetyl-4-hydroxy-3-[1-(p-hydroxyphenylamino)ethylidene]-2H-pyran-2,6(3H)-dione, m.p. 223°–225° C. Both the mono-and di-sodium salts are prepared upon treatment of the dione with sodium methoxide in methanol.

Similarly, m-hydroxyaniline and o-hydroxyaniline are reacted with an equimolar amount of 3,5-diacetyl-4,6-dihydroxy-2H-pyran-2-one in methanol to give the respective products, 5-acetyl-4-hydroxy-3-[1-(m-hydroxyphenylamino)ethylidene]-2H-pyran-2,6(3H)-dione, m.p. 213°–216° C., and 5-acetyl-4-hydroxy-3-[1-(o-hydroxyphenylamino)ethylidene]-2H-pyran-2,6(3H)-dione, m.p. 210°–212° C.

EXAMPLE 6 p-Fluoroaniline (2.2 g., 0.02 m.) is added to a hot solution of 4.24 g. (0.02 m.) of 3,5-diacetyl-4,6-dihydroxy-2H-pyran-2-one in 150 ml. of methanol. The mixture is refluxed overnight and filtered to give 5-acetyl-3-[1-(p-fluorophenylamino)ethylidene]-4-hydroxy-2H-pyran-2,6-(3H)-dione, m.p. 199°–201° C.

EXAMPLE 7

A mixture of 2.12 g. of 3,5-diacetyl-4,6-dihydroxy-2H-pyran-2-one, 1.25 g. of p-aminothiophenol and 75 ml. of methanol is refluxed for two hours, cooled and filtered to yield 5-acetyl-4-hydroxy-3-[1-(p-mercaptophenylamino)ethylidene]-2H-pyran-2,6(3H)-dione, m.p. 207°–210° C.

EXAMPLE 8

To a boiling solution of 3.0 g. (0.014 m.) of 3,5-diacetyl-4,6-dihydroxy-2H-pyran-2-one in 25 ml. of benzene is added 1.4 g. (0.015 m.) of aniline and the resulting mixture is refluxed overnight. The reaction mixture is cooled and filtered to give 5-acetyl-4-hydroxy-3-[1-phenylamino)ethylidene]-2H-pyran-2,6(3H)-dione, m.p. 184°–186° C.

Similarly, equimolar amounts of p-methoxyaniline and 3,5-diacetyl-4,6-dihydroxy-2H-pyran-2-one are refluxed in methanol to give, upon workup, 5-acetyl-4-hydroxy-3-[1-(p-methoxyphenylamino)ethylidene]-2H-pyran-2,6(3H)-dione, m.p. 212°–214° C.

EXAMPLE 9 o-Phenylenediamine (2.1 g., 0.02 m.) is added to a hot solution of 4.2 g. (0.02 m.) of 3,5-diacetyl-4,6-dihydroxy-2H-pyran-2-one in methanol and the resulting mixture is refluxed for two hours. The reaction mixture is cooled and filtered to yield 5-acetyl-3-[1-(o-aminophenylamino)ethylidene]-4-hydroxy-2H-pyran-2,6(3H)-dione, m.p. 179°–181° C.

Similarly, reaction of an equimolar amount of p-phenylenediamine as described above gives the corresponding 5-acetyl-3-[1-(p-aminophenylamino)ethylidene]-4-hydroxy-2H-pyran-2,6(3H)-dione, m.p. 215°–218° C.

EXAMPLE 10

To a solution of 3.03 g. (0.01 m.) of 5-acetyl-4-hydroxy-3-[1-(p-hydroxyphenylamino)ethylidene]-2H-pyran-2,6(3H)-dione, 1.0 g. (0.01 m.) of triethylamine in 150 ml. of tetrahydrofuran is added 0.78 g. (0.01 m.) of acetyl chloride. The resulting mixture is refluxed for two hours, cooled and filtered. The solid is recrystallized to give 3-[1-(p-acetoxyphenylamino)ethylidene]-5-acetyl-4-hydroxy-2H-pyran-2,6(3H)-dione, m.p. 199°–201° C.

Similarly, equimolar amounts of 5-acetyl-4-hydroxy-3-[1-(p-hydroxyphenylamino)ethylidene]-2H-pyran-2,6-(3H)-dione and an appropriate alkanoyl chloride are reacted as described above to give the following alkanoyloxy derivatives:

5-acetyl-4-hydroxy-3-[1-(p-propionyloxyphenylamino)ethylidene]-2H-pyran-2,6(3H)-dione, m.p. 168°–170° C;

5-acetyl-3-[1-(p-butyryloxyphenylamino)ethylidene]-4-hydroxy-2H-pyran-2,6(3H)-dione, m.p. 158°–160° C.;

5-acetyl-4-hydroxy-3-[1-(p-pentanoyloxyphenylamino)ethylidene]-2H-pyran-2,6(3H)-dione, m.p. 155°–157° C;

5-acetyl-3-[1-(p-hexanoyloxyphenylamino)ethylidene]-4-hydroxy-2H-pyran-2,6(3H)-dione, m.p. 148°–149° C.;

5-acetyl-3-[1-(p-heptanoyloxyphenylamino)ethylidene]-4-hydroxy-2H-pyran-2,6(3H)-dione, m.p. 147°–148° C.

EXAMPLE 11

To a boiling solution of 2.1 g. (0.01 m.) of 3,5-diacetyl-4,6-dihydroxy-2H-pyran-2-one in 150 ml. of methanol is added 2.4 g. (0.01 m.) of p-(N-benzylcarbamoyloxy)aniline and the resulting mixture is refluxed for one hour. The cooled reaction mixture is filtered and the solid is recrystallized to furnish 5-acetyl-3-[1-(p-N-benzylcarbamoyloxyphenylamino)ethylidene]-4-hydroxy-2H-pyran-2,6(3H)-dione, m.p. 195°–197° C.

EXAMPLE 12

A solution of 1.88 g. (0.01 m.) of p-carbamoyloxyaniline hydrochloride and 1.0 g. (0.01 m.) of triethylamine in 50 ml. of methanol is added to a hot solution of 2.21 g. (0.01 m.) of 3,5-diacetyl-4,6-dihydroxy-2H-pyran-2-one in 150 ml. of methanol. The resulting mixture is refluxed for two hours, cooled and filtered solid recrystallized to give 5-acetyl-3-[1-(p-carbamoyloxyphenylamino)ethylidene]-4-hydroxy-2H-pyran-2,6(3H)-dione, m.p. 213°–215° C.

Similarly, reaction with p-(N-methylcarbamoyloxy)-aniline or p-(N,N-dimethylcarbamoyloxy)-aniline as described above or in Example 11 yields the corresponding products, namely 5-acetyl-4-hydroxy-3-[1-(p-N-methylcarbamoyloxyphenylamino)ethylidene]-2H-pyran-2,6(3H)-dione and 5-acetyl-3-[1-(p-N,N-dimethylcarbamoyloxyphenylamino)ethylidene]-4-hydroxy-2H-pyran-2,6(3H)-dione.

EXAMPLE 13

A solution of 1.5 g. (0.01 m.) of p-ureidoaniline in 50 ml. of methanol is added to a solution of 2.1 g. (0.01 m.) of 3,5-diacetyl-4,6-dihydroxy 2H-pyran-2-one in 150 ml. of methanol. A solid is formed immediately and the mixture is refluxed for 12 hours. The filtered solid is recrystallized to give 5-acetyl-4-hydroxy-3-[1-(p-ureidophenylamino)ethylidene]-2H-pyran-2,6(3H)-dione, m.p. 250°–253° C.

As a specific embodiment of a useful composition of this invention, an active ingredient such as 5-acetyl-4-hydroxy-3-[1-(n-propylamino)ethylidene]-2H-pyran-2,6(3H)-dione is dissolved in sterile water at a concentration of 0.5% and aerosolized from a nebulizer operating at an air flow adjusted to deliver the desired aerosolized weight of drug.

For oral administration, compositions such as those in the following examples can be prepared.

EXAMPLE 14

| Ingredients | Mg./Tablet |
|---|---|
| 5-Acetyl-4-hydroxy-3-[1-(p-hydroxyphenylamino)ethylidene]-2H-pyran-2,6(3H)-dione | 10 |
| Calcium sulfate, dihydrate | 150 |
| Sucrose | 25 |
| Starch | 15 |
| Talc | 5 |

| Ingredients | Mg./Tablet |
|---|---|
| Stearic acid | 3 |

The sucrose, calcium sulfate and active ingredient are thoroughly mixed and granulated with hot 10% gelatin solution. The wetted mass is passed through a No. 6 mesh screen directly onto drying trays. The granules are dried at 120° F. and passed through a No. 20 mesh screen, mixed with the starch, talc and stearic acid, and compressed into tablets.

EXAMPLE 15

| Ingredients | Mg./Capsule |
|---|---|
| 5-Acetyl-4-hydroxy-3-[1-(p-hydroxyphenylamino)ethylidene]-2H-pyran-2,6(3H)-dione | 50 |
| Magnesium stearate | 5 |
| Lactose | 350 |

The above ingredients are screened through a No. 40 mesh screen, mixed and filled into No. 0 hard gelatin capsules.

EXAMPLE 16

To a mixture of 12 ml. of formic acid and 20 ml. of acetic anhydride (which has been stirred at room temperature for 45 minutes) is added 5 g. (0.036 m.) of p-nitroaniline. After stirring for five hours at room temperature, the reaction mixture is filtered to give p-nitroformanilide, m.p. 195°–199° C. The latter, 3 g. (0.018 m.), is hydrogenated at room temperature in a mixture of 150 ml. of ethanol and 0.3 g. of 10% palladium-on-carbon in a Parr apparatus until the calculated amount of hydrogen is absorbed. The catalyst is filtered off and the solvent is removed in vacuo to leave p-aminoformanilide.

To a boiling solution of 2.67 g. (0.0123 m.) of 3,5-diacetyl-4,6-dihydroxy-2H-pyran-2-one in 50 ml. of methanol is added 1.8 g. (0.0123 m.) of p-aminoformanilide. Additional methanol is added (30 ml.) and reflux is continued for 40 minutes. The reaction mixture is filtered and the solid recrystallized to yield 5-acetyl-3-[1-(p-formamidophenylamino)ethylidene]-4-hydroxy-2H-pyran-2,6 (3H-dione, m.p. 247°–248° C. (dec.).

Similarly, following the procedures described above 3,5-diacetyl-4,6-dihydroxy-2H-pyran-2-one is condensed with an appropriate amino substituted anilide to give the following alkanoylamino derivatives:

5-acetyl-4-hydroxy-3-[1-(p-isobutyramidophenylamino)ethylidene]-2H-pyran-2,6 (3H)-dione, m.p. 357°–358° C. (dec.);

5-acetyl-3-[1-(o-formamidophenylamino)ethylidene]-4-hydroxy-2H-pyran-2,6(3H)-dione, m.p. 197°–198° C. (dec.);

5-acetyl-3-[1-(m-acetamidophenylamino)ethylidene]-4-hydroxy-2H-pyran-2,6-(3H)-dione, m.p. 220°–221° C. (dec.)

5-acetyl-4-hydroxy-3-[1-(m-propionamidophenylamino)ethylidene]-2H-pyran-2,6-(3H)-dione, m.p. 202°–203° C. (dec.);

5-acetyl-3-[1-(m-butyramidophenylamino)ethylidene]-4-hydroxy-2H-pyran-2,6(3H)-dione, m.p. 193°–194° C. (dec.);

5-acetyl-4-hydroxy-3-[1-(m-isobutyramidophenylamino)ethylidene]-2H-pyran-2,6(3H)-dione, m.p. 219°–221° C. (dec.).

An advantageous compound, 5-acetyl-3-[1-(m-acetamidophenylamino)ethylidene]-4-hydroxy-2H-pyran-2,6(3H)-dione, produced 65% inhibition of the rat PCA wheal at 0.25 mg/kg, i.v., and upon oral administration produced 53% inhibition at 25 mg/kg and a pretreatment time of 15 minutes.

EXAMPLE 17

A methanolic solution of 1.00 g. (0.0047 m.) of 3,5-diacetyl-4,6-dihydroxy-2H-pyran-2-one and 65 mg. (0.0242 m.) of p-aminophenoxyacetic acid is refluxed for 30 minutes, cooled and filtered to give 5-acetyl-3-[1-(p-carboxymethyleneoxyphenylamino)ethylidene]-4-hydroxy-2H-pyran-2,6(3H)-dione, m.p. 213°–214° C.

What is claimed is:

1. A pharmaceutical composition for inhibiting the symptoms of asthma comprising a nontoxic pharmaceutical carrier or diluent and an amount sufficient to produce said inhibition of a compound represented by the formula:

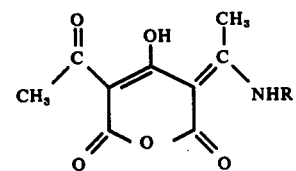

wherein R is lower alkyl, straight or branched chain, of from 3 to 6 carbon atoms, phenyl, halophenyl, hydroxyphenyl, methoxyphenyl, alkanoyloxyphenyl, the alkanoyl moiety having from 2 to 7 carbon atoms, carbamoyloxyphenyl, N-methylcarbamoyloxyphenyl, N-benzylcarbamoyloxyphenyl, N,N-dimethylcarbamoyloxyphenyl, p-mercaptophenyl, aminophenyl, alkanoylaminophenyl, the alkanoyl moiety having from 2 to 5 carbon atoms, carboxymethyleneoxyphenyl or ureidophenyl, or a monoor di-alkali metal salt of said compound.

2. A pharmaceutical composition according to claim 1 in a form suitable for administration by inhalation.

3. A pharmaceutical composition according to claim 1 comprising a solution or suspension of the active ingredient in sterile water.

4. A pharmaceutical composition according to claim 1 in the form of an aerosol formulation.

5. A pharmaceutical composition according to claim 1 in which the pharmaceutical carrier or diluent is a solid.

6. A pharmaceutical composition according to claim 1 in which R is n-propyl, p-mercaptophenyl, hydroxyphenyl, p-acetoxyphenyl, p-pentanoyloxyphenyl, p-aminophenyl, m-alkanoylaminophenyl or p-ureidophenyl.

7. A pharmaceutical composition according to claim 6 in which R is m-acetamidophenyl.

8. A pharmaceutical composition according to claim 6 in which R is p-hydroxyphenyl.

9. A pharmaceutical composition according to claim 6 in which R is p-aminophenyl.

10. A pharmaceutical composition according to claim 1 in dosage unit form and in which the active ingredient is in an amount of about 0.5 mg. to about 500 mg. per dosage unit.

11. A compound represented by the formula:

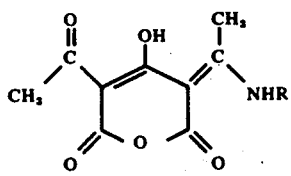

wherein R is lower alkyl, straight or branched chain, of from 3 to 6 carbon atoms, hydroxyphenyl, alkanoyloxyphenyl, the alkanoyl moiety having from 2 to 7 carbon atoms, carbamoyloxyphenyl, N-methylcarbamoyloxyphenyl, N-benzylcarbamoyloxyphenyl, N,N-dimethylcarbamoyloxyphenyl, p-mercaptophenyl, aminophenyl, alkanoylaminophenyl, the alkanoyl moiety having from 2 to 5 carbon atoms, carboxymethyleneoxyphenyl, or ureidophenyl, or a mono-or di-alkali metal salt of said compound.

12. A compound according to claim 11 in which R is hydroxyphenyl.

13. A compound according to claim 12 in which R is p-hydroxyphenyl.

14. A compound according to claim 12 in the form of a disodium salt.

15. A compound according to claim 11 in which R is p-aminophenyl.

16. A compound according to claim 11 in which R is m-alkanoylaminophenyl.

17. A compound according to claim 16 in which R is m-acetamidophenyl.

18. A compound according to claim 16 in which R is m-propionamidophenyl.

19. A compound according to claim 11 in which R is p-carboxymethyleneoxyphenyl.

20. The method of inhibiting the symptoms of asthma which comprises administering to an animal in need thereof a therapeutically effective amount for producing said inhibition of a compound represented by the formula:

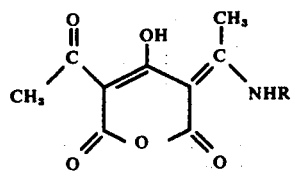

wherein R is lower alkyl, straight or branched chain, of from 3 to 6 carbon atoms, phenyl, halophenyl, hydroxyphenyl, methoxyphenyl, alkanoyloxyphenyl, the alkanoyl moiety having from 2 to 7 carbon atoms, carbamoyloxyphenyl, N-methylcarbamoyloxyphenyl, N-benzylcarbamoyloxyphenyl, N,N-dimethylcarbamoyloxyphenyl, p-mercaptophenyl, aminophenyl, alkanoylaminophenyl, the alkanoyl moiety having from 2 to 5 carbon atoms, carboxymethyleneoxyphenyl or ureidophenyl, or a mono- or di-alkali metal salt of said compound.

21. The method of claim 20 in which the active ingredient is administered in a daily dosage regimen of about 0.5 mg. to about 2000 mg.

* * * * *